US00PP34972P2

(12) United States Plant Patent
Horvath

(10) Patent No.: US PP34,972 P2
(45) Date of Patent: Feb. 7, 2023

(54) ***RUDBECKIA* PLANT NAMED 'SWEET AS HONEY'**

(50) Latin Name: ***Rudbeckia* hybrid**
Varietal Denomination: Sweet as Honey

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/300,764

(22) Filed: Oct. 29, 2021

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell

(57) ABSTRACT

A new and distinct variety of *Rudbeckia* plant as illustrated and described, characterized by the combination of smaller foliage, shorter height and lighter yellow flowers compared to the seed parent.

1 Drawing Sheet

Figure 1:
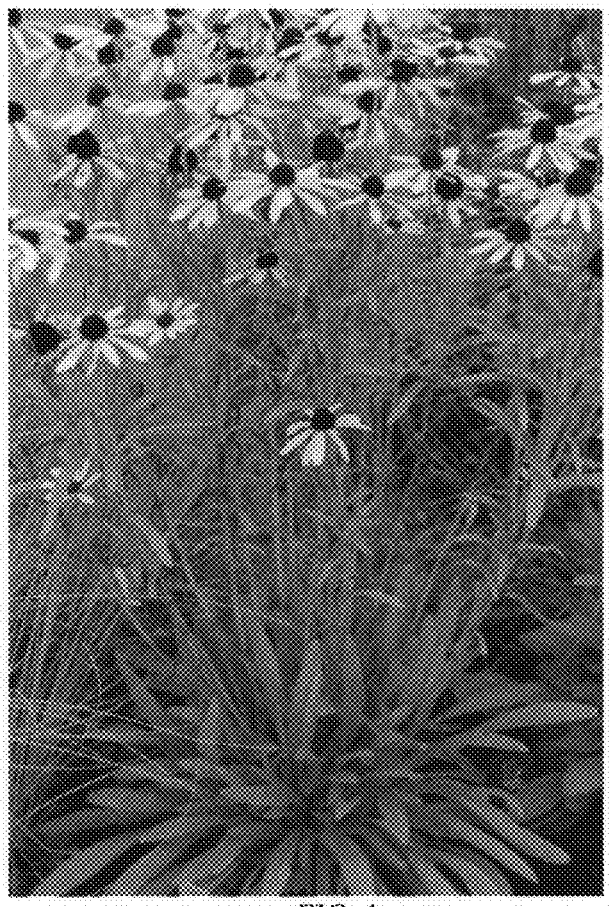

Latin name: *Rudbeckia* hybrid.
Cultivar name: 'Sweet as Honey'.

BACKGROUND OF THE INVENTION

The present invention relates to a new and distinct hybrid of *Rudbeckia* plant named 'Sweet as Honey' characterized by the combination of smaller hairy foliage, shorter height and, yellow flowers compared to the seed parent. The new *Rudbeckia* was raised as a seedling from open pollinated seed sown from the seed parent, an unnamed plant of *Rudbeckia missouriensis*, not patented, in Hebron, Ill. in 2017. The selection of the new plant was due to its' smaller hairy foliage, shorter height & lighter yellow flowers compared to the seed parent. Initial asexual reproduction has taken place at a nursery in Hebron, Ill. since 2018 by means of division, and stem cuttings. The new *Rudbeckia* has shown to be stable and identical in reproduction to the originally discovered plant after rooting over 700 plants from 2018 to 2021. No plants of the new *Rudbeckia* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Rudbeckia* plant named 'Sweet as Honey' characterized by the combination of smaller hairy foliage, shorter height and yellow flowers, have been observed to be unique and stable. For purpose of comparison the new plant will be referred to as 'Sweet as Honey'.

'Sweet as Honey' can be compared to plants of *Rudbeckia missouriensis* the seed parent, unnamed, not patented. 1. The new *Rudbeckia* plant has a mature size measuring 55 cm high and 45 cm wide while *Rudbeckia missouriensis* measures 75 cm high and over 60 cm wide. 2. The new *Rudbeckia* plant has a naturally upright shaped habit while

*Rudbeckia missouriensis* has an upright open habit 3. The new *Rudbeckia* plant has smaller foliage approximately 20 cm long and 17 mm wide while *Rudbeckia missouriensis* has foliage that reaches approximately 30-35 cm long and 5 cm wide.

'Sweet as Honey' can also be compared to the *Rudbeckia* 'American Gold Rush' patented, U.S. Plant Pat. No. 28,498. 1. The new plant has smaller and thinner foliage, 20 cm in length and 17 mm wide while *Rudbeckia* 'American Gold Rush' has foliage 25 cm long and 5 cm wide. 2. The new plant has a yellow flower color RHS 14 A while *Rudbeckia* 'American Gold Rush' plant has a gold flower color RHS 17 A.

'Sweet as Honey' can also be compared to the *Rudbeckia fulgida* 'Little Gold Star' patented, U.S. Plant Pat. No. 22,397.

1. The new plant has longer and thinner foliage, 20 cm in length and 17 mm wide while *Rudbeckia fulgida* 'Little Gold Star' has foliage 9 cm long and 3.8 cm wide.
2. The new plant has a yellow flower color RHS 14 A while *Rudbeckia fulgida* 'Little Gold Star' plant has a gold flower color RHS 17 A-C.

DESCRIPTION OF PHOTOGRAPHS

Figure 2:
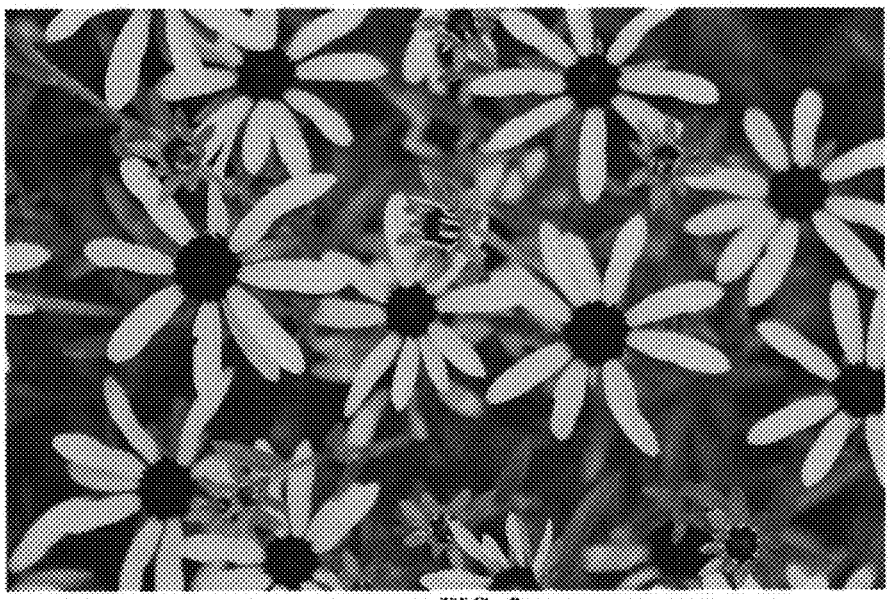

FIG. 1. A blooming 2 year old plant in July.
FIG. 2. A close up of the flowers.

DETAILED BOTANICAL DESCRIPTION

In the following description, color references are made to The Royal Horticultural Society Colour Chart 2001 edition. Plants used for the description were grown for two seasons at a nursery in Hebron, Ill. Measurements and numerical values represent averages of typical plants.

Botanical classification: *Rudbeckia* cultivar Sweet as Honey.

Parentage: Male or pollen parent an unknown *Rudbeckia*, female or seed parent an unnamed plant of *Rudbeckia missouriensis*.

Propagation: Vegetative division and stem cutting propagation.

Root description: Fibrous, medium thickness, brown in color.

Root habit: Moderate branching, moderate density.

Plant description: Herbaceous perennial. Overall habit of the new *Rudbeckia* is a mound shaped clump, with branching stems topped by yellow inflorescences starting in July.

*Plant height.*—55 cm.

*Plant width.*—45 cm.

*Primary stem diameter.*—4 mm.

*Primary and secondary stem description.*—Branching, with 10 or more leaves. Leaves get smaller as they go up the stem. Strength — strong.

*Primary and lateral stem texture.*—Pubescent with hairs up to 1-2 mm long.

*Secondary stem description.*—Average 5 lateral stems per primary stem.

*Secondary stem length.*—25 cm.

*Secondary stem diameter.*—2-3 mm.

*Secondary stem internodes.*—5 cm.

*Stem color.*—Both 144 B and 144 C.

Foliage:

*Type.*—Herbaceous.

*Leaf arrangement.*—Alternate, simple, sessile.

*Basal foliage length.*—20 cm Width — 17 mm.

*Stem foliage length.*—7-9 cm Width — 8 mm.

*Shape.*—Lanceolate.

*Apex.*—Acute.

*Base.*—Cuneate.

*Margin.*—Entire.

*Texture.*—Pubescent, soft.

*Venation.*—Pinnate. Venation Color 145 B.

*Adaxial leaf description.*—Color is 137 C including developing, fully expanded.

*Abaxial leaf description.*—Color is 146 B including developing, fully expanded.

Bud:

*Bud shape.*—Oblate.

*Bud length.*—5 mm.

*Bud diameter.*—9 mm.

*Bud color.*—Close to 146 B.

Inflorescence:

*Inflorescence type.*—Single, composite on branched flowering stems.

*Position.*—Borne on both terminal and axillary peduncles above the foliage.

*Number of inflorescences per plant.*—Approximately 160.

*Arrangement.*—Disc and ray florets.

*Mature center disc.*—15 mm wide and 8 mm height.

*Number of disc florets.*—200, number of ray florets 13.

*Immature disc floret color.*—146 B.

*Mature disc floret color.*—Dark brown but close to 200 A.

*Disc floret diameter.*—1-2 mm at apex, 1 mm at base.

*Disc floret shape.*—Rotate.

*Disc floret length.*—3 mm. Disc floret width — 1 mm.

*Disc floret apex.*—Acute.

*Disc floret margin.*—Entire.

*Ray floret size.*—3 cm length and 8 mm width.

*Ray floret color upon opening and in full bloom.*—Adaxial 14 A and Abaxial 13 C.

*Ray floret aspect.*—Initially incurved, then upright, then perpendicular to the peduncle.

*Ray floret shape.*—Lanceolate.

*Ray floret apex.*—Emarginate.

*Ray floret base.*—Obtuse.

*Ray floret margin.*—Entire.

*Ray floret count.*—Approximately 13 per inflorescence.

*Ray floret texture.*—Both the upper and lower surfaces are smooth, glabrous.

*Overall inflorescence size.*—7 cm or more across in diameter with ray florets, 1 cm in height. Receptacle height — 4-5 mm, diameter 1 cm across.

*Bloom period and duration.*—Mid July through September. 5-7 weeks on the plant.

*Blooming habit.*—Domed, upright on 55 cm terminal flowering stems.

Phyllaries:

*Number of phyllaries per inflorescence.*—16 average.

*Length.*—12 mm. Width — 3-4 mm.

*Shape.*—Lanceolate.

*Apex.*—Mucronate.

*Base.*—Fused.

*Margin.*—Entire.

*Texture.*—Both upper and lower surface scattered pubescence.

*Color.*—Adaxial 137 B and Abaxial 137 C.

Peduncles:

*Length of both terminal and axillary peduncles.*—25 cm.

*Diameter.*—2-3 mm.

*Angle.*—Erect to about 15-20 degrees from vertical.

*Strength.*—Strong, Texture — pubescent, Color — both 144B and 144C.

Reproductive organs:

*Androecium.*—Quantity per disc floret, 5.

*Filament length.*—3-4 mm. Filament color 145 C.

*Anther shape.*—Oblong. Anther length — 1 mm.

*Anther color.*—14 A.

*Pollen amount.*—Slight but present.

*Pollen color.*—11 D.

*Gynoecium present on ray and disc florets.*—

*Pistils.*—One, length 3 mm.

*Stigma shape.*—Two parted, Stigma color — 200 A.

*Style length.*—4 mm, Style color — 200 A.

*Scent.*—No scent noticed.

Seed and fruit: None observed.

Disease resistance: Resistance to diseases common to *Rudbeckia* has not been observed on plants grown under nursery conditions.

Insect resistance: Resistance to insects common to *Rudbeckia* has not been observed on plants grown under nursery conditions.

Hardiness: Plants of the new *Rudbeckia* have been observed to be hardy to USDA Zone 5.

I claim:

1. A new and distinct variety of *Rudbeckia* plant named 'Sweet as Honey' as illustrated and described, characterized by the combination smaller foliage, shorter height, and yellow flowers compared to the seed parent.

* * * * *